United States Patent [19]

Watson et al.

[11] Patent Number: 5,208,026

[45] Date of Patent: May 4, 1993

[54] COMPOSITION FOR BIOCONTROL OF PLANTAIN

[75] Inventors: Alan K. Watson, Pincourt; Guy Tourigny; Richard S. Winder, both of Ile Perrot, all of Canada

[73] Assignee: The Royal Institution for the Advancement of Learning, Quebec, Canada

[21] Appl. No.: 475,950

[22] Filed: Feb. 6, 1990

[51] Int. Cl.⁵ .......................... C12N 1/00; A01N 63/00
[52] U.S. Cl. ............................. 424/93 Q; 435/911; 504/117
[58] Field of Search ............... 424/93; 71/79; 435/911

[56] References Cited

U.S. PATENT DOCUMENTS 5,028,253  7/1991  Watson et al. .......................... 71/79

FOREIGN PATENT DOCUMENTS 1224055  7/1987  Canada .................................. 424/93

*Primary Examiner*—Douglas W. Robinson
*Assistant Examiner*—L. Blaine Lankford
*Attorney, Agent, or Firm*—Cushman, Darby & Cushman

[57] ABSTRACT

The present invention is concerned with a novel bioherbicide and its use to control *Plantago major* plantain. More specifically, the invention is concerned with Colletotrichum sp. G1 having the identifying characteristics of culture deposit No. ATCC 20980. The present invention is also concerned with a method for suppressing growth of plants of plantain in turfed and agricultural areas.

5 Claims, 1 Drawing Sheet

COMPOSITION FOR BIOCONTROL OF PLANTAIN

PRIOR ART

The *Plantago major* (Plantain) can be described as an annual, biennial, or perennial herb. It produces a rosette of glabrous or pubescent, ovate to elliptic leaves with entire or slightly toothed margins. Its fruit is a capsule bearing 4-22 seeds which are dark-brown and highly variable in shape.

Plantain is said to mar the appearance of lawns, gardens, roadsides, and waste places. It is also found in damp shorelines, open woods, and pastures. In local situations, it can reduce the early growth of crops such as corn and oats. Plantain may be the host of aster yellows disease and is used as a transient host by the pear psylla, *Psylla pyricola*.

Plantain is closely associated with the activity of man. It is widely distributed throughout the world, even at high elevations (2800 m in Valais, Switzerland). It has a truly remarkable wide range of distribution as it occurs from pole to pole, although apparently absent from the lowland tropics. It is clearly cosmopolitan.

Plantain occurs on a very wide range of soil types such as loam, clay and sand. It is a common species of cultivated soil, waste ground and roadsides.

The growing season in Northern areas of U.S.A. occurs from mid-April to late October. Flowering can be continuous over mid-June to October, with a peak in July. Plantain is a long day plant and flowering fails unless the photoperiod is greater than 13 hours. The fruits mature 2-3 weeks after anthesis. Seeds are always viable and germinate intermittently throughout the growing season. Plantain is easily spreaded, since it is wind pollinated and capable of full self-fertilization.

It is known that longevity of seed sin soils is at least 21 years. Longevity in dry storage is less than 10 years. Seed viability has been shown to be about 80%. Light appears to be a necessary germination requirement, and either chilling or higher temperature regimes, or both can increase germination. Plantain benefits also from mowing, as the competitive effect of taller vegetation is temporarily removed.

It is common knowledge that plantain is susceptible to a variety of chemical herbicides such as 2,4-D, MCPA, fenoprop, 2,4-DB, MCPB, dicamba and combinations of various broadleaf herbicides.

Normally, plantain is easily controlled in lawns through chemical methods. However, there is mounting public pressure to reduce the wide-spread use of herbicides in lawns because of contamination of the environment and of reports of herbicide-related health problems amongst city dwellers exposed to herbicide applications.

Risks of enviromental contamination are high when one considers that only between 0.1 and 5.0 percent of pesticides reach their target pest. The remainder is carried by air and taken up by the soil fauna and flora, to become part of the food chain, and enters aquatic habitats and water systems. Several studies show that residues of a variety of pesticides have been detected in human serum, urine, adipose tissue and human milk. There is large evidence for the adverse health effects of pesticides. Pesticide-related cancer and respiratory diseases are occupational hazard for agricultural workers.

It would therefore be highly desirable to develop a product which would be highly effective in controlling the growth of plantain, and which would not have the pollutant drawbacks and health hazards of the chemical herbicides presently used to that effect.

SUMMARY OF THE INVENTION

In accordance with the present invention, there is now provided a new composition for biocontrol of plantain, which comprises of the fungus Colletotrichum sp. G1 having the identifying characteristics of culture deposit No. ATCC 20980, in association with an agriculturally acceptable carrier.

The present invention is also concerned with a method for biological control of weeds. More specifically, the method of the present invention involves the application of a fungal pathogen Colletotrichum sp. G1 having the identifying characteristics of culture deposit No. ATCC 20980 on areas infested with *Plantago major* L.(Broad-leaved plantain), and allows one to control plantain without undesirable effects to the environment.

Finally, the present invention is concerned with a novel Colletotrichum sp. G1 characterized as having the property of controlling *Plantago major*, and when in its essentially pure form, has the taxonomic characterization of culture deposit No. ATCC 20980.

IN THE DRAWING:

FIG. 1 describes the pathogenic effect of Colletotrichum sp. G1 on plantain.

DETAILED DESCRIPTION OF THE INVENTION

Figure 1:

In accordance with the present invention, there is now provided an alternative to chemical control of plantain in the form of a composition comprising a fungal plant pathogen.

More specifically, the present invention comprises the use of a novel fungus Colletotrichum sp. G1, which has the identifying characteristics of the culture deposit No. ATCC 20980 to control plantain.

Use of mycoherbicides is generally recognized as being highly desirable when employed against weeds, since they are safe to the environment (non-toxic), target specific, and safe to human health. Since the fungus Colletotrichum sp. G1 of the present invention is indigenous to North America, it is deemed not hazardous to existing ecosystems (non-disruptive).

Although mycoherbicides have shown their usefulness in agricultural settings none are as yet available for use in urban environments against plantain.

A subculture of Colletotrichum sp. G1 has been deposited in the permanent collection of the American Type Culture Collection, Rockville, Md., U.S.A., on Feb. 5, 1990 under the Budapest Treaty. The culture was assigned the accession number ATCC 20980 by the repository. The deposit is available to the public upon the grant of a patent disclosing it. However, it should be understood that the availability of the deposit does not constitute a license to practice the subject invention in derogation of patent rights granted by governmental action.

Isolation

The original isolate of the fungal of the present invention was obtained from plants grown for experimental purposes in our controlled-environment cabinets. These plants developed disease symptoms without any intervention, which implies that the disease is also seed transmitted. The isolation technique used was that commonly employed in plant pathology in which diseased leaf tissue is immersed in 70% ethanol for a few seconds, transferred to 1.5% sodium hypochlorite for approximately 15 seconds, and rinsed with sterile water. After drying on filter paper, the leaf pieces are placed on a suitable growth medium (e.g. V8, MEA, etc.). For storage, the isolated strain was grown on a PDA slant in a screw-cap glass vial and placed in a refrigerator.

DESCRIPTION OF SYMPTOMS AND DAMAGE

Preliminary laboratory tests have shown that the pathogen Colletotrichum sp. G1 can heavily damage plantain (FIG. 1). Under appropriate conditions, the fungus Colletotrichum sp. G1 causes a severe blight of older leaves within 36 to 72 hours after inoculation. The leaves and petioles dry up, shrivel, and whither. These take up a greyish velvety appearence. Milder symptoms include chlorisis, leaf pitting, dark-brown to greyish lesions and light shrivelling. Although 80% of the leaves may die out the plant generally recovers by producing new leaves and resumes growth, though the final growth achieved is short of that of untreated, healthy plants.

DESCRIPTION OF COLONY AND SPORES

Colonies grow radially and have a yeast-like appearance. The color is buff to light brown and the texture smooth. Spores are produced in abundance over the whole surface of the colony in a matrix substance. The colony forms a hump in the center and sometimes a ring of protruding fused hyphae. The spores are hyaline, one-celled, and ovoid to elongate in shape.

The fungus of the present invention is used in concentration of from about $10^5$ to $10^8$ conidia/ml. Preferred application ratio are from about $10^6$ to $10^9$ conidia/$m^2$. The composition of the present application is prepared by admixing an aqueous suspension of conidia with a suitable carrier. The composition is then applied to the surface of an area containing undesirable plantain. Preferably, the composition is applied as a spray.

The following Examples are given to illustrate the present invention, and are not to be construed as limiting its scope.

EXAMPLE I

This example illustrates the production and preparation of inoculum for applying onto plantain. New starter or seed cultures are begun by placing a small piece of mycelium transferred from a stored culture onto the centre of a Petri plate. Production plates are obtained by transferring mycelial plugs from the seed cultures three to five days later. Five mycelial plugs are placed onto each plate to ensure rapid coverage of the medium's surface. The production plates are harvested after two to three weeks of growth at room temperature on the lab bench.

Harvesting is done by pouring 15 ml of tap water onto each plate and by scraping the spores using a spatula. The solution is then filtered through a layer of nylon mesh to remove agar and mycelial particles. A spore count using a hemacytometer is then made and the volume adjusted to yield the desired spore concentration. This method usually gives spore yields of 1.1 to $1.5 \times 10^8$ spores/ml. The spores are then applied to the plants either by spraying or by brushing.

Several growth media were found suitable for the production of spores. Table 1 shows the spore yields obtained from four different growth media. The fungus does not grow well on PDA (Potato Dextrose Agar) and Bacto-Agar media.

TABLE 1

Effect of culture medium on the production of spores.

| Growth Medium | Spore yield (spores/ml) |
| --- | --- |
| Cornmeal | $6.06 \times 10^7$ |
| V8 | $3.85 \times 10^7$ |
| Malt Extract Agar | $6.22 \times 10^7$ |
| Carrot Agar | $8.00 \times 10^4$ |

EXAMPLE II

This example illustrates the effect of formulation or application method on disease development. The experiment consisted of four treatments replicated four times each, one pot per replicate, three plants per pot. Plants at the 2 to 3 leaf stage were sprayed or brushed with solutions of $10^8$ spores/ml. After treatment the plants were subjected to a dew period of 24 hours at 21° C. The plants were then placed in a growth cabinet set at 21° C. day/18° C. night with a 16 hour photoperiod. Percent leaf area damaged (LAD) was measured five days, and fresh weight and dry weight were measured four weeks, after inoculation. The results of the experiment are shown in Table 2. The control treatment consisted of plants sprayed with a 1% Paraffin solution. Paraffin did not cause damage or appear to have any effect on plant growth when compared to untreated plants of the same cohort. Visual examination of inoculated plant four weeks after treatment showed a clear depression in growth and symptoms of chlorosis. Fresh weight and dry weight were reduced by all treatment with the bioherbicide.

TABLE 2

Effect of formulation or application method on disease development.

| Treatment | % LAD | Fresh Weight (g) | Dry Weight (g) |
| --- | --- | --- | --- |
| Control[a] | 0.25 | 5.356 | 0.729 |
| Paraffin 1%[b] | 22.5 | 3.489 | 0.495 |
| Sprayed[b] | 37.5 | 2.675 | 0.477 |
| Brushed[b] | 20.0 | 3.708 | 0.602 |

[a]Control treatment consisted of plants sprayed with 1% paraffin solution.
[b]Treatments consisted of spore concentration of $10^8$ spores/ml.

EXAMPLE III

This example illustrates the effect of leaf wetness duration and air temperature during the first 24 hours of the infection process on disease development. The leaf wetness duration experiment consisted of 3 treatments (18, 24 and 30 hours), replicated 2 times with one pot per replicate and 3 plants per pot. The air temperature experiment consisted of 3 treatments (21° C., 24° C., and 27° C.), replicated 4 times with one pot per replicate and 3 plants per pot. All plants in this experiment were at the 2 to 3 leaf stage. All treated plants were inoculated with a spore solution containing $10^8$ spores/ml. Control plants (sprayed with water only) were not affected by any of the treatments. Tables 3 and 4 show the results for these 2 experiments. Percent leaf area damaged was measured 3 days after inoculation. These results demonstrate that greater damages to plantain was obtained at cooler temperature and dew period of 24 hours.

TABLE 3

Effect of air temperature on disease development.

| Temperature | % LAD |
|---|---|
| 21° C. | 34.6 |
| 24° C. | 14.3 |
| 27° C. | 6.0 |

TABLE 4

Effect of leaf wetness duration on disease development.

| Dew Period | % LAD |
|---|---|
| 18 hours | 4.3 |
| 24 hours | 39.2 |
| 30 hours | 30.0 |

What is claimed is:

1. A method for controlling the growth of the Plantain, *Plantago major,* which method comprises applying to the plaintain or locus of the plaintain an effective amount of the isolated fungus Colletotrichum sp. G1 having the identifying characteristics of culture deposit No. ATCC 20980, to cause lesions so as to depress growth or kill said plaintain.

2. A composition for controlling the growth of the Plantain, *Plantago major* comprising an effective amount of the fungus Colletotrichum sp. G1 having the identifying characteristics of culture deposit No. ATCC 20980, in association with an agriculturally acceptable carrier.

3. A substantially biologically pure culture of Colletotrichum sp. G1 characterized as having the property of controlling *Plantago major,* and having the taxonomic characterization of culture deposit No. ATCC 20980.

4. A composition according to claim 2, wherein the concentration of the fungus is from $10^5$ to $10^8$ conidia/ml of carrier.

5. A composition according to claim 4, wherein the composition is applied by spraying, at a a ratio of from $10^6$ to $10^9$ conidia/m$^2$.

* * * * *